(12) United States Patent
Fikatas et al.

(10) Patent No.: US 11,013,512 B2
(45) Date of Patent: May 25, 2021

(54) DEVICE FOR SEPARATING TISSUE PARTS

(71) Applicant: CHARITÉ—UNIVERSITÄTSMEDIZIN BERLIN, Berlin (DE)

(72) Inventors: Panagiotis Fikatas, Berlin (DE); Igor Sauer, Berlin (DE); Marcus Bahra, Berlin (DE)

(73) Assignee: CHARITÉ —UNIVERSITÄTSMEDIZIN BERLIN, Berlin (DE)

( * ) Notice: Subject to any disclaimer, the term of this patent is extended or adjusted under 35 U.S.C. 154(b) by 273 days.

(21) Appl. No.: 15/751,582

(22) PCT Filed: Aug. 12, 2016

(86) PCT No.: PCT/EP2016/069233
§ 371 (c)(1),
(2) Date: Feb. 9, 2018

(87) PCT Pub. No.: WO2017/025626
PCT Pub. Date: Feb. 16, 2017

(65) Prior Publication Data
US 2018/0235628 A1   Aug. 23, 2018

(30) Foreign Application Priority Data

Aug. 12, 2015 (DE) ...................... 10 2015 113 307.5

(51) Int. Cl.
*A61B 17/00* (2006.01)
*A61B 17/072* (2006.01)
(Continued)

(52) U.S. Cl.
CPC .... *A61B 17/07207* (2013.01); *A61B 18/1442* (2013.01); *A61B 18/085* (2013.01);
(Continued)

(58) Field of Classification Search
CPC ...... A61B 2017/07285; A61B 18/1442; A61B 2018/1452; A61B 17/07207
(Continued)

(56) References Cited

U.S. PATENT DOCUMENTS

| 5,599,350 A | 2/1997 | Schulze et al. |
| 5,797,938 A | 8/1998 | Paraschac et al. |

(Continued)

FOREIGN PATENT DOCUMENTS

| DE | 44 21 822 C1 | 10/1995 |
| DE | 199 51 940 C2 | 11/2001 |

(Continued)

OTHER PUBLICATIONS

International Search Report dated Nov. 16, 2016, dated Nov. 15, 2016.
(Continued)

*Primary Examiner* — Chelsea E Stinson
(74) *Attorney, Agent, or Firm* — Norris McLaughlin, P.A.

(57) ABSTRACT

The invention relates to a device for separating tissue parts, wherein the device has two parallel clamping plates, wherein at least one part of one clamping plate can be pivoted away from the other clamping plate in order to receive a tissue part and can be pivoted back in order to fix the tissue part, wherein the device has at least two interconnected blades arranged at an angle to each other or has one curved or kinked blade, wherein the blade or blades is/are insertable and displaceable in guide rails of the clamping plates, and wherein a cutting edge of the blade or blades extends between the clamping plates.

20 Claims, 7 Drawing Sheets

Figure 1:
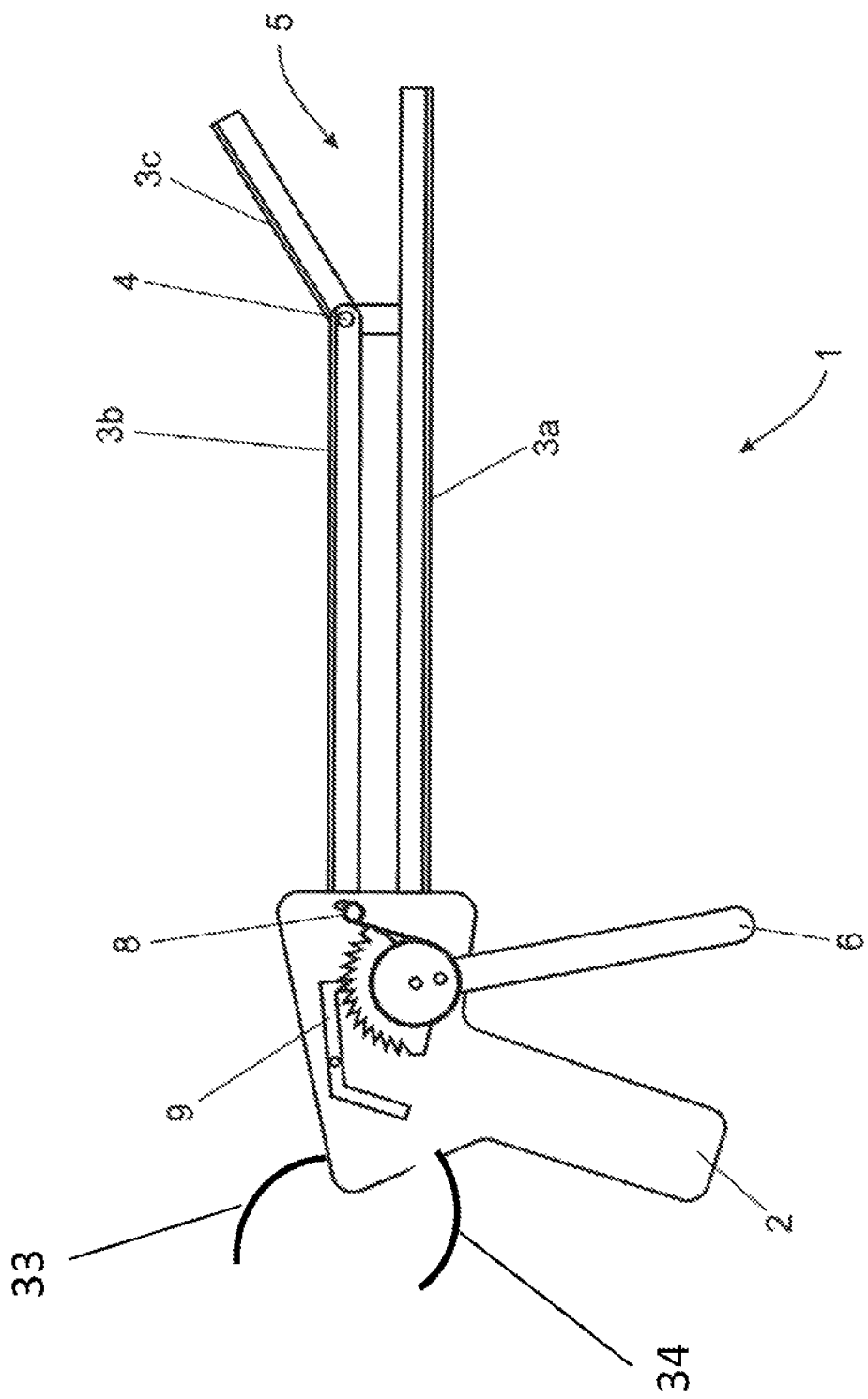

(51) Int. Cl.
*A61B 18/14* (2006.01)
*A61B 17/32* (2006.01)
*A61B 18/00* (2006.01)
*A61B 17/29* (2006.01)
*A61B 18/08* (2006.01)

(52) U.S. Cl.
CPC .............. *A61B 2017/00884* (2013.01); *A61B 2017/07214* (2013.01); *A61B 2017/07271* (2013.01); *A61B 2017/07278* (2013.01); *A61B 2017/07285* (2013.01); *A61B 2017/2946* (2013.01); *A61B 2017/320075* (2017.08); *A61B 2017/320082* (2017.08); *A61B 2018/00589* (2013.01); *A61B 2217/007* (2013.01)

(58) Field of Classification Search
USPC ...................................................... 227/180.1
See application file for complete search history.

(56) References Cited

U.S. PATENT DOCUMENTS

| | | | |
|---|---|---|---|
| 5,797,941 A * | 8/1998 | Schulze | A61B 18/1442 606/171 |
| 2007/0073340 A1 | 3/2007 | Shelton, IV et al. | |
| 2007/0083234 A1 * | 4/2007 | Shelton, IV | A61B 17/07207 606/219 |
| 2010/0030248 A1 | 2/2010 | Palmer et al. | |
| 2016/0228145 A1 * | 8/2016 | Gleiman | A61B 17/320092 |
| 2017/0333064 A1 * | 11/2017 | Ebner | A61B 17/072 |

FOREIGN PATENT DOCUMENTS

| | | |
|---|---|---|
| DE | 10 2015 113 307 A1 | 2/2017 |
| JP | H-06237936 A | 8/1994 |
| JP | H-06327684 A | 11/1994 |
| JP | 2010-504810 A | 4/2007 |
| KR | 10-1444058 B1 | 9/2014 |
| WO | 2013/130859 A1 | 9/2013 |
| WO | 2015/053905 A1 | 4/2015 |

OTHER PUBLICATIONS

English Translation of International Search Report dated Nov. 16, 2016, dated Nov. 15, 2016.
German Search Report corresponds to German Application No. 10 2015 113 307.5 dated Apr. 11, 2016.
English translation of Office Action dated Sep. 3, 2020, in connection with Japanese Application No. 2018-507505.

* cited by examiner

DEVICE FOR SEPARATING TISSUE PARTS

The invention relates to a device for separating tissue parts.

Linear staplers are used in surgery to separate tissue portions. The operating principle consists of compressing the tissue between two metal plates to the maximum extent, adapting the ends with tangential staples and separating it with a centrally extending blade.

Due to its mode of operation, a linear stapler can only be advantageously used in the case of flat tissue structures such as e.g. an intestine, so that linear staplers have proven themselves in gastrointestinal tract surgery. Solid organs are mostly separated manually with the aid of coagulation of the resection surfaces. In the case of rigid and voluminous organs (e.g. the liver, kidney, pancreas, uterus) it has been shown that linear staplers resulted in ruptures far beyond the resection margin as a result of squeezing of the tissue by the metal plates. This results in intraoperative or postoperative bleeding which has a high probability of fistula formation.

Since linear staplers are only available in minimally invasive surgery, the resection of solid organs has hitherto taken place using open or hybrid techniques. During the separation of solid organs, the priorities are avoiding shear forces caused by squeezing the tissue and securely closing the resection edge. It is possible to resect large tissue pieces without creating large resection surfaces using the "fish-mouth technique". In this case, the resection is not performed linearly, rather the tissue is separated in the shape of a wedge. This produces resection margins in the shape of a fish mouth. Adapting these margins makes it possible to completely cover the resection surface inwardly. Hitherto, the complexity of the resection in the "fish-mouth technique" has only allowed this technique to be used in open operations.

DE 199 51 940 C2 discloses a clamping sewing apparatus which can be used in open surgery and endoscopy, having an action grip and a clamping head, said clamping sewing apparatus being connected to Bowden cables extending in a hollow shaft, wherein the hollow shaft can be removed.

The object of the invention is to improve the separation of solid organs as well, both in open and in minimally invasive surgery.

This object is achieved with a device according to claim 1. Advantageous configurations are set out in the subordinate claims.

The device according to the invention for separating tissue parts comprises two parallel clamping plates, wherein at least one part of one clamping plate can be pivoted away from the other clamping plate in order to receive a tissue part and can be pivoted back in order to fix the tissue part, at least two interconnected blades arranged at an angle to each other or one curved or kinked blade, wherein the blade or blades is/are insertable and displaceable in guide rails of the clamping plates, and wherein a cutting edge of the blade or blades extends between the clamping plates.

The advantage of the device according to the invention is that a separation of solid organs as well can be accomplished mechanically, without the resection margin being squeezed, thus avoiding the risks indicated above. The stapler described herein can simplify operating procedures or respectively significantly extend the present range of operations, particularly in minimally invasive surgery, during which linear staplers have hitherto been used due to the lack of alternatives. The separation of solid organs using the device according to the invention with edge sealing using the "fish-mouth technique" makes it possible to separate solid organs safely and with a reduced risk of complications. The operating time is significantly reduced by the mechanical resection. In addition to open surgery, the instrument can also be used in minimally invasive surgery. The current resection possibilities of solid organs are significantly restricted, particularly in minimally invasive operations, due to a lack of instrumentation. The device presented here could make possible minimally invasive operations which have hitherto only been feasible using open techniques.

The device according to the invention can also be referred to as a stapler or linear stapler. The clamping plates preferably have a rectangular and/or narrow clamping surface. One or both or respectively a part of one or both clamping plates is/are designed to be pivotable. The blades can be fixedly connected to each other, for example by a welding operation. On the other hand, an angular or V-shaped blade having two partial blades or respectively having an angular cutting edge or one or more arc-shaped blades can be provided. The distance of the clamping plates can be adjustable, so that these can be adapted to different tissue parts.

The blade or blades can be directly insertable and displaceable in the guide rails or fixedly or displaceably arranged in a cutting insert, wherein the cutting insert is insertable and displaceable in the guide rails. This makes it possible to adjust the device in many ways, for example for different intended purposes.

The two blades, which each have a blade body and a cutting surface, are arranged at an angle $\alpha$ to each other. This means that the angle $\alpha$ is generated between the lateral surfaces, which are inclined to each other, of the blades of the blade bodies of the two blades. Alternatively, a blade can also be used, which is preferably kinked centrally at an angle $\alpha$. The angle $\alpha$ can be within a range between 40° and 150°, preferably 90°. This angle $\alpha$ makes possible a resection of the tissue/organ part using the fish-mouth technique with small resection surfaces. This means that the tissue piece/organ part to be removed is separated from the organ in the shape of a wedge.

The cutting surfaces of the two blades can form a cutting edge. An intersection point is created at the point at which the two cutting surfaces of the blades meet each other. This intersection point of the two blades can be aligned above the outer ends of the two blades or can be offset. This means that the cutting edge of the two blades can be arranged such that this defines an angle ß to the perpendicular through the intersection point of the blades. The angle ß can be within a range of 0 to 80°. Consequently, the intersection point of the two blades can be set back or placed in front in the region of the clamping plates or of the cutting insert with respect to the outer surfaces of the blades. The intersection point of the two blades can also be designated the vertex of the angles $\alpha$ and/or ß or the apex of the angle. The outer ends of the blades are then located at endpoints of legs of the angle $\alpha$. The outer ends are guided in the guide rails of the clamping plates, resulting in a more stable separation with a clean cutting edge, because the outer ends separate the tissue first. Alternatively, the intersection point of the two blades can be upstream or placed in front so that the intersection point separates the tissue first. This configuration can be advantageous in certain applications. Optionally, a more stable, for example thicker, blade can then be provided.

The tissue can already be separated by pushing the blades forward in the closed position. Furthermore, the opening of the cutting edge, packing of the tissue and closing (meeting) of the blades make it possible to separate the tissue at the longitudinal edge of the blades.

The cutting insert can have recesses in the region facing away from the cutting edge. These recesses can be designed in such a manner that they are at least partially arranged in the region of the cutting insert, the blades and/or a base body of the cutting insert, which engages in the guide rails of the clamping plates. As a result, the guiding region of the cutting insert is shortened, simplifying the insertion and/or the removal of the cutting insert.

The cutting insert can have a base body which is insertable in the guide rails of the clamping plates and displaceable in the latter, and which has receptacles for fastening or displaceably receiving the blade or blades. The base body can improve the handling of the cutting insert, since the blade or the blades do/does not then have to be directly touched.

The blade or blades can have a power connection for thermal coagulation and/or for an ultrasound unit for thermal coagulation and/or ultrasonic dissection. This facilitates the separation procedure and improves the resection result.

The device can have a staple cartridge having staples arranged perpendicularly or at a different angle to the clamping plates. The staples can consist of a metal material. The staples can be pretensioned so that, following release, they staple the resection margins without additional forces being applied. Alternatively or additionally, the staple insert can exert a force on the staples, in order to close the latter.

The staple cartridge can be directly insertable and displaceable in the guide rails or can be fixedly or displaceably arranged in a staple insert, wherein the staple insert is insertable and displaceable in the guide rails. This makes it possible to adjust the device in many ways, for example for different intended purposes.

The staple insert can have pins extending parallel to the clamping plates for closing, wherein the pins are displaceably arranged for contacting the staples or the pins contact the staples via closing elements. This allows simultaneous or virtually simultaneous stapling in one work step, thus simplifying the work process.

The staple cartridge and/or the staple insert can have at least one channel with openings for providing a fluid or a granulate. The result of the operation can be significantly improved by adding or injecting coagulation-promoting or respectively fibrin-forming substances, which reduce the tendency to bleed and encourage healing. In addition, it is possible to use a two-component (2C) or multiple-component adhesive in order to bond or seal the resection surfaces.

The device can have a grip part, to which the clamping plates are fastened and a grip of the grip part is set up to pivot the at least one part of one clamping plate. The grip part can have the form of a revolver grip. The grip part facilitates the handling of the device.

The staples can be arranged under tension and can be automatically closable after being released. This closure without the application of an external force can simplify the construction.

The blade or the blades and the staple cartridge can be arranged axially behind each other in the guide rails. Both elements can, in this case, also be provided as a connected unit. The blade and the staple cartridge can then be pushed behind each other through the guide rails and pushed out of them at the front.

The distance of the pivotable part of a clamping plate from the other clamping plate can be adjustable. Thus, for example, in an articulation, for example as in the case of a pipe wrench, both the opening angle and the distance of the two closed clamping plates, which then extend parallel, can be adjusted. This makes possible adaptation for different intended purposes.

An articulation which can be angled can be provided in the region of the two parallel clamping plates. Consequently, the device can be adapted to different insertion angles. The articulation can be arranged between the grip and the pivot joint. This is a space-saving solution which nevertheless provides a large working area.

Figure 2:
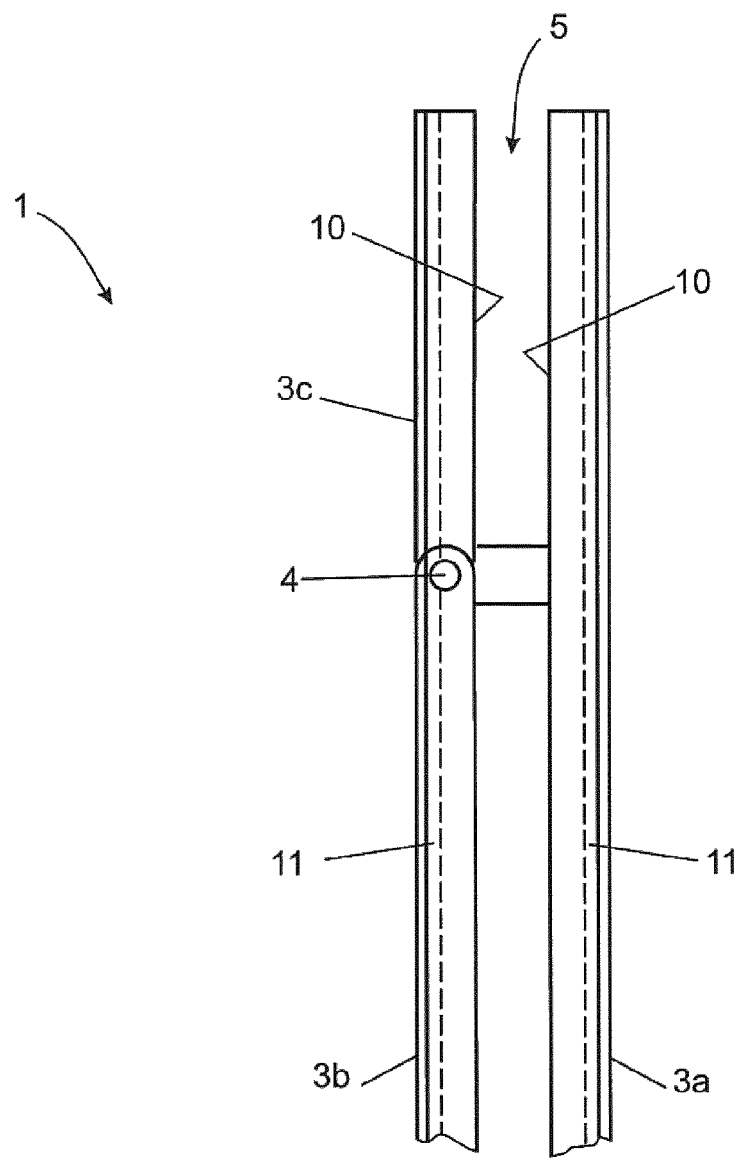
Figure 3:
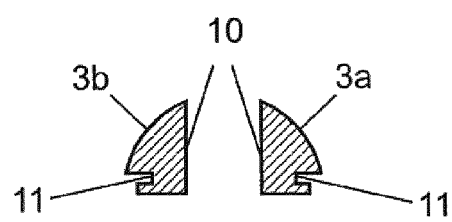
Figure 4:
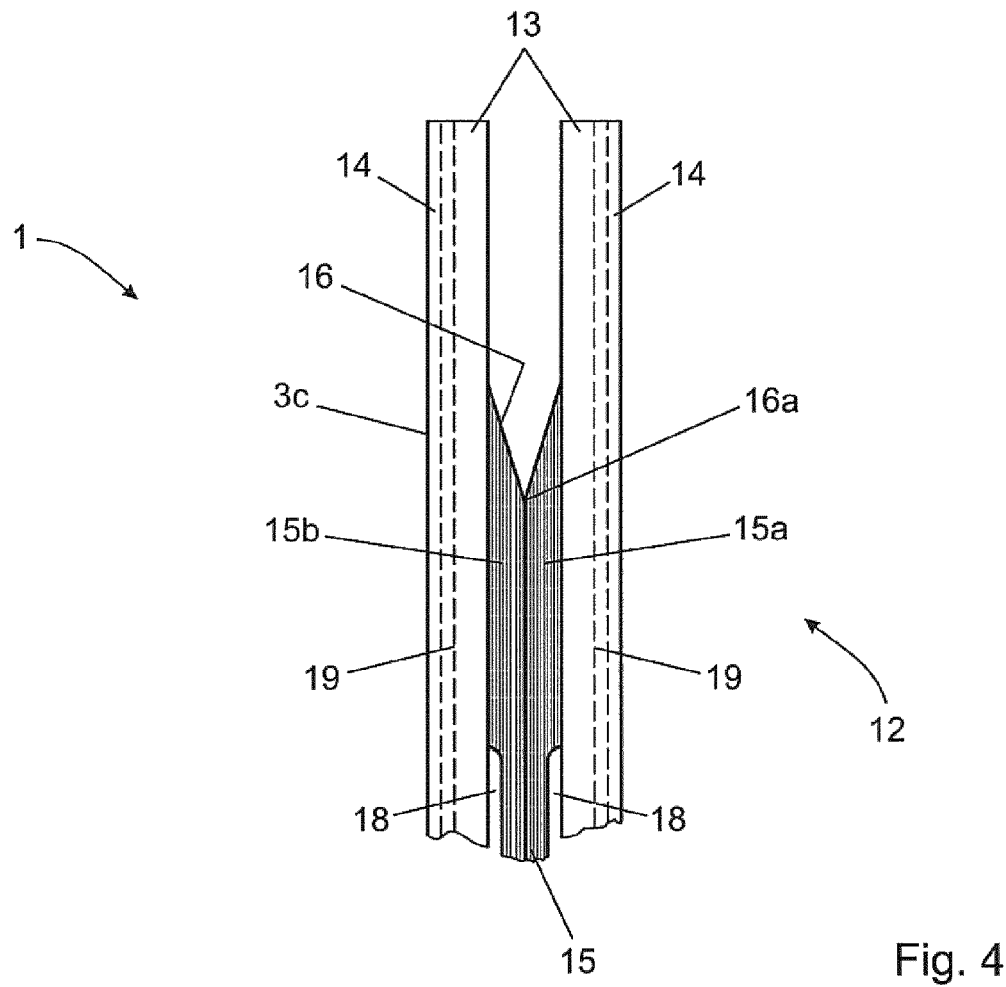
Figure 5:
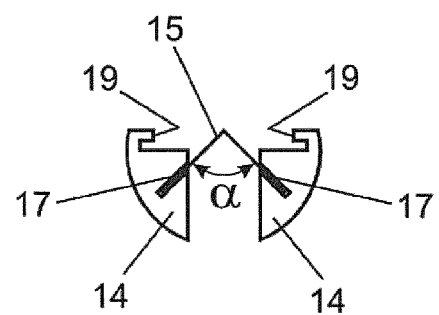
Figure 6:
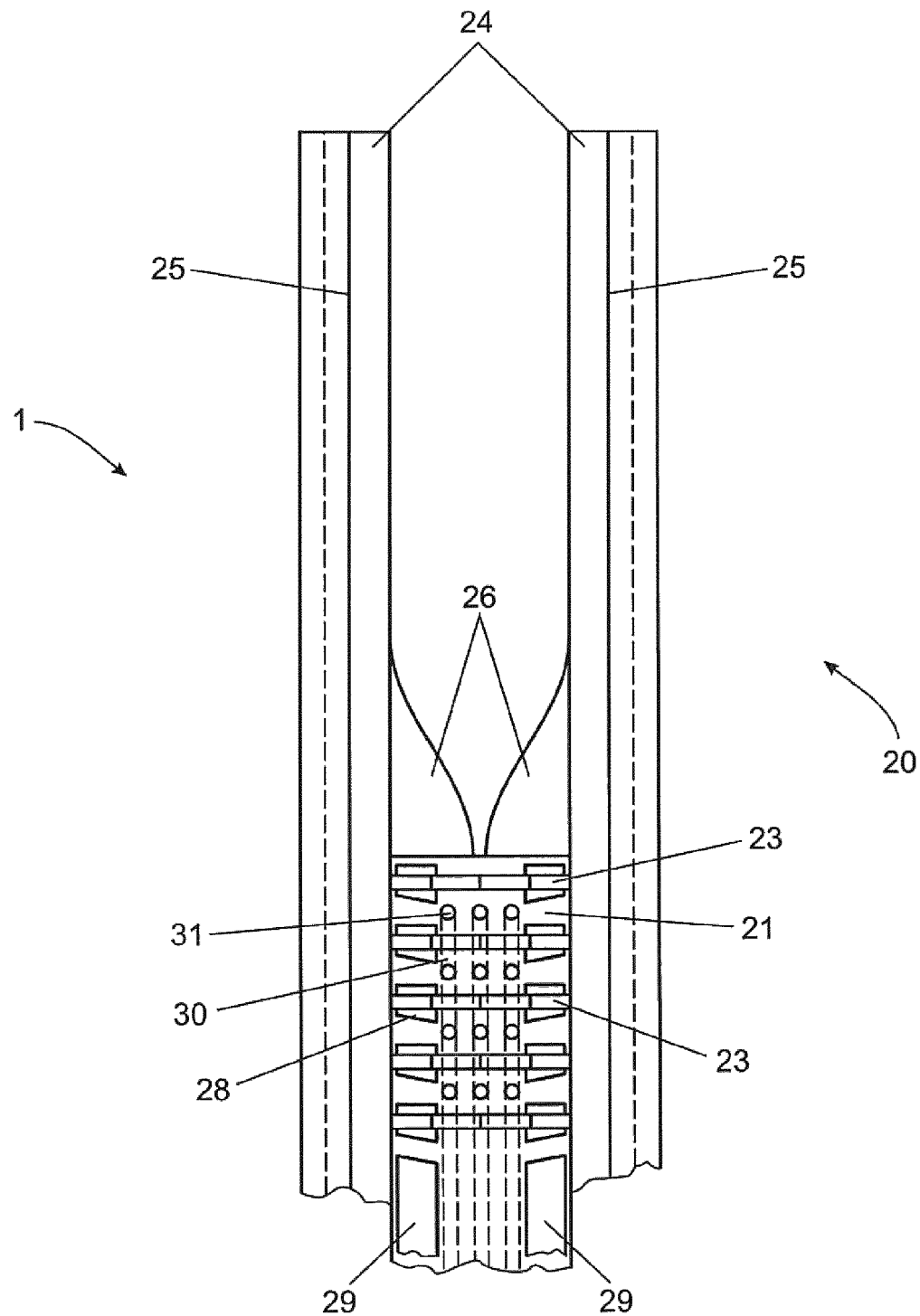
Figure 7:
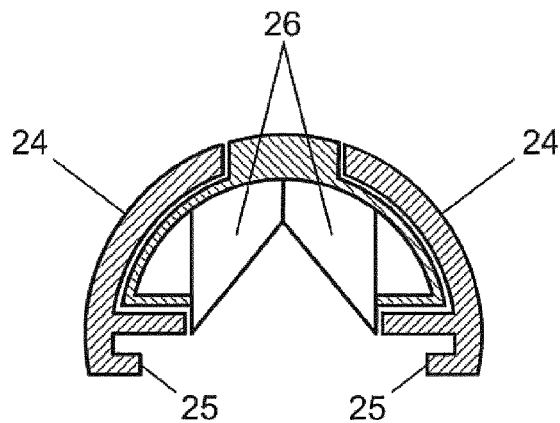
Figure 8:
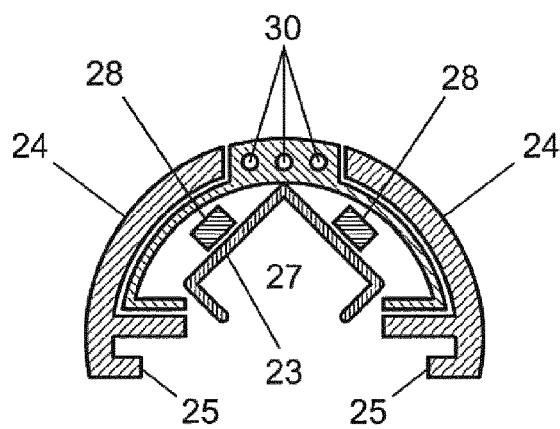
Figure 9:
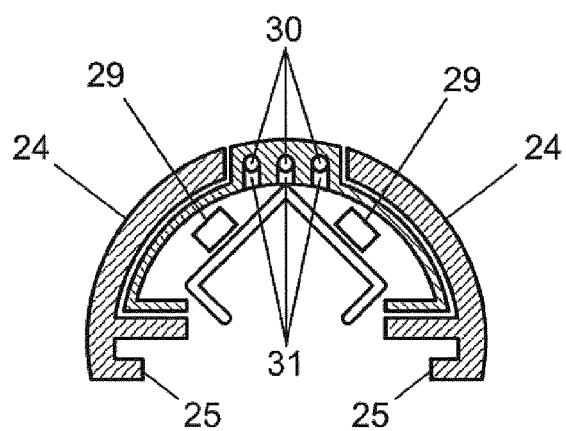
Figure 10:
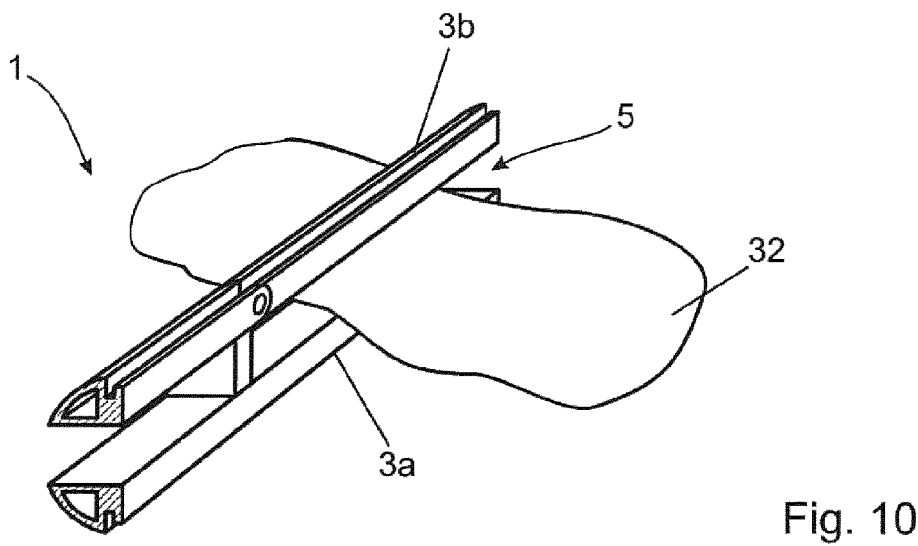
Figure 11:
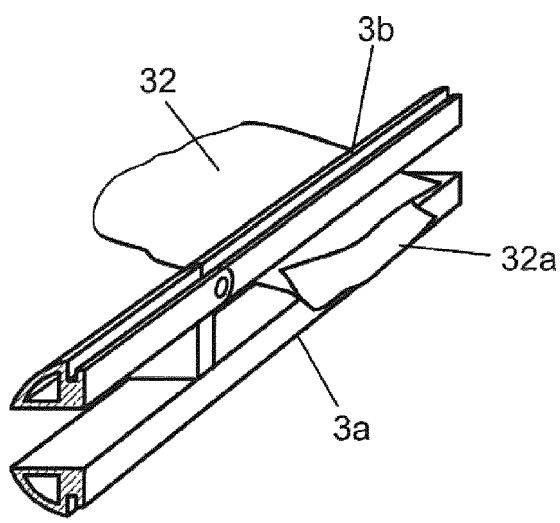
Figure 12:
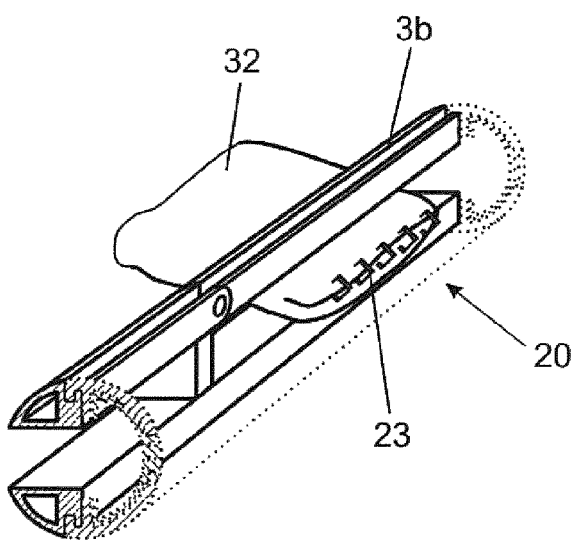
Figure 13:
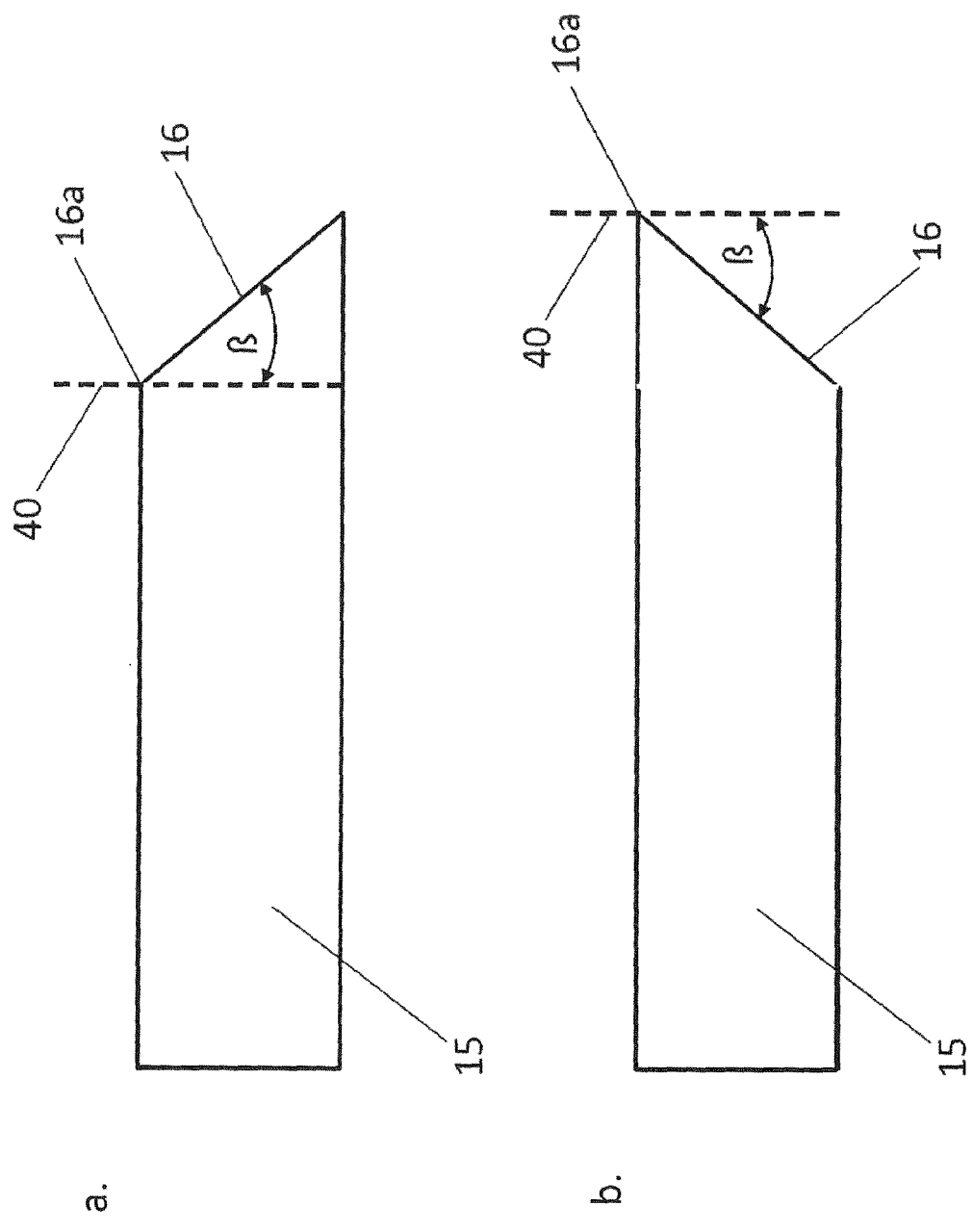

The invention will be explained below in embodiment examples with reference to the associated drawings, wherein:

FIG. 1 shows a schematic representation of an embodiment example of a device for separating tissue parts, FIG. 2 shows a schematic representation of another embodiment example of a device for separating tissue parts, FIG. 3 shows a cross-sectional view of the device from FIG. 2, FIG. 4 shows a schematic representation of a cutting insert of the device, FIG. 5 shows a cross-sectional view of the cutting insert from FIG. 2, FIG. 6 shows a schematic representation of a staple insert of the device, FIG. 7 shows a first cross-sectional view of the staple insert from FIG. 6, FIG. 8 shows a second cross-sectional view of the staple insert from FIG. 6, FIG. 9 shows a third cross-sectional view of the staple insert from FIG. 6, FIG. 10 shows a perspective representation of the device with a fixed tissue part, FIG. 11 shows a perspective representation of the device with a separated tissue part, FIG. 12 shows a perspective representation of the device with a stapled tissue part, and FIGS. 13a and 13b show a lateral view of a blade e.g. for a cutting insert from FIG. 4.

FIG. 1 shows a device 1 for separating tissue parts, in particular tissue parts of solid or rigid organs such as e.g. the liver, kidney, pancreas, uterus, etc. The device 1 comprises a grip part 2, to which two parallel clamping plates 3a and 3b are fastened. At least one part or region 3c of a clamping plate, here the clamping plate 3b, is pivotably supported by means of a hinge 4. A rotational axis of the hinge or articulation 4 is perpendicular to a longitudinal extension of the clamping plates 3a and 3b. The part 3c of the clamping plate 3b can be pivoted away from the other clamping plate 3a in order to receive a tissue part and can be pivoted back in order to fix the tissue part. Consequently, a receiving space 5 is formed between the clamping plate 3a and the pivotable part 3c of the other clamping plate 3b, which receiving space can be opened and closed in a similar manner to forceps, said opening and closing being realized by the pivoting movement of the part 3c.

The pivotable part 3c is moved by means of a grip 6 of the grip part 2. The grip 6 and the pivotable part 3c are interconnected, by way of example, by means of a Bowden cable 8 or at least a metal strut. A latching or locking mechanism 9 can lock the pivotable part 3c in each position. The locking mechanism 9 is configured to be detachable.

The clamping plates 3a and 3b, which can also be referred to as the stapler head or part of a stapler head, will now be described more precisely with reference to FIGS. 2 and 3. In FIG. 2, the stapler head having the two clamping plates 3a and 3b is shown in the closed position. Consequently, the two clamping plates 3a and 3b also extend parallel in the clamping region 5. Each clamping plate 3a and 3b comprises a clamping surface 10, wherein the two clamping surfaces 10 of the two clamping plates 3a and 3b face each other. In the closed state, these clamping surfaces 10 produce a defined, but not complete compression of tissue which is located in the clamping region 5 between the two clamping plates 3a and 3b. The clamping is not used to separate or initially separate the tissue, but merely to fix the tissue in the stapler head. The clamping surfaces 10 and/or the clamping plates 3a and 3b have an elongated or respectively rectangular form. They have a narrow configuration, i.e. the width is small compared to the length.

Each clamping plate 3a and 3b comprises a guide rail 11, said guide rails extending parallel to each other. In this specification, the term "parallel" also encompasses the open state of the device 1, i.e. including the situation where the part 3c of the clamping plate 3b is pivoted open and does not therefore actually extend parallel to the other clamping plate 3a. Since, however, the remaining part of the clamping plate 3b and also the part 3c extend parallel in the closed state, the term "parallel" is used here in the context of this specification.

The guide rails 11 are arranged on the surfaces of the clamping plates 3a and 3b facing away from the clamping surfaces 10. Alternatively, they can be configured on surfaces which adjoin the clamping surfaces 10.

A cutting insert of the device 1 will now be described in more detail with reference to FIGS. 4 and 5, which cutting insert can be inserted in the guide rails 11 of the clamping plates 3a and 3b and can be displaced in the latter. The cutting insert 12 comprises a base part or base body 13 with two parallel plates 14. A blade 15 is provided between the plates 14, which blade consists of two interconnected blades 15a and 15b arranged at an angle to each other. The blade 15 can be configured in one part or can be assembled from the two blades 15a and 15b. The two plates 14 are fixedly connected to each other towards the grip side 2. The blade 15 or respectively the blades 15a and 15b has/have a cutting edge 16 for separating tissue which is arranged in the clamping region 5 of the device 1.

As can be seen in FIG. 5, the blade 15 is fastened or axially movable in receptacles 17 of the plates 14. The fastening in the receptacles 17 can be effected by clamping and/or bonding. The two blades 15a and 15b are arranged at an angle α to each other. The angle α here has a value between 60° and 120° and preferably has a value of 90°. The angle α and the blade 15 are configured in such a manner that the blade 15 is arranged in a V-shape between the two plates 14. In the orientation represented in FIGS. 4 and 5, the blade points upwards. This means that, depending on the angle α and lengths of the blades 15a and 15b, the intersection point of the two blades 15a and 15b is located above or below the receptacles 17 or respectively the plates 14.

In the case of the cutting edge 16, an intersection point 16a of the two blades 15a and 15b is set back compared to the outer ends of the two blades 15a and 15b, which are arranged in the receptacles 17 of the plates 14. The term "set back" refers to an axial or longitudinal direction of the cutting insert 12 or respectively the device 1. The longitudinal direction extends in the direction of the parallel clamping plates 3a and 3b or respectively the plates 14. On a rear side or a region facing away from the cutting edge 16, the cutting insert 12 or respectively the blade 15 and/or the plate 14 has/have recesses 18. With the aid of these recesses 18, the blade 15 can be removed more easily from the cutting insert 12, or respectively the cutting insert 12 can be removed more easily from the clamping plates 3a and 3b.

In order to insert the cutting insert in the clamping plates 3a and 3b, the plates 14 of the cutting insert 12 contain guide rails 19 which are designed to complement the guide rails 11 of the clamping plates 3a and 3b. This means that the guide rails 11 and 19 can engage in each other so that the cutting insert 12 is displaceably guided in the clamping plates 3a and 3b. The cutting insert 12 and, in particular, the blade 15 or respectively the receptacles 17 are configured in such a manner that the blade 15 engages, on an axial displacement of the cutting insert 12 in the clamping plates 3a and 3b, in the clamping region 5.

A power connection 33 and an ultrasound unit connection 34 of the blade 15 or respectively the blades 15a and 15b is optionally provided as shown in FIG. 1, which ensures thermal coagulation and/or ultrasonic dissection during the process of cutting through the tissue.

FIGS. 13a and 13b respectively show a two-part blade 15 for a cutting insert of the device 1 in a lateral view. The cutting surfaces of the two blades form the cutting edge 16, wherein the intersection point 16a is located at the point at which the cutting surfaces of the two blades meet each other. The cutting edge 16 is arranged at an angle ß to the perpendicular 40 through the intersection point 16a. FIG. 13a shows how the intersection point 16a of the two-part blade 15 is set back by the angle ß relative to the outer end of the blade 15. Here, the term "set back" refers to an axial or longitudinal direction of the cutting insert 12 from FIG. 4. FIG. 13b shows a two-part blade 15 having an angle 11, as a result of which the intersection point 16a forms the outer end of the blade 15.

An optional staple insert 20 of the device 1 will be described with reference to FIGS. 6 to 9, which staple insert, like the cutting insert 12, is insertable in the clamping plates 3a and 3b and is displaceable in the latter. The staple insert 20 contains a staple cartridge 21 having staples 23 for stapling resection surfaces or resection margins of tissue parts which are located in the clamping region 5 of the device 1. The staple cartridge 21 is held between plates 24 or respectively connects the latter. The plates 24 correspond to the plates 14 of the cutting insert 12. Accordingly, the plates 24 have guide rails 25 which correspond to the guide rails 12 of the cutting insert 19 and are designed to complement the guide rails 11 of the clamping plates 3a and 3b. Consequently, the staple insert 20 can be inserted in the clamping plates 3a and 3b and can be displaced in the latter.

Two or more of the staples 23 can be interconnected in the manner of, for example, a hair clip. This means that they can engage in each other or be connected by means of one or more articulations.

In a front region, that is to say facing the clamping region 5, the staple insert 20 contains two adaptation surfaces 26 which serve to bring the tissue edges together following the wedge-shaped resection. The adaptation surfaces 26 or respectively the interior or the space between the two adaptation surfaces 26 is/are designed in the shape of a funnel or respectively a wedge, in order to bring together the tissue edges. This cross-section is represented in FIG. 7.

The staple cartridge 21 is arranged behind the adaptation surfaces 26. Immediately following the adaptation surfaces 26 is a first staple 23 of the staple cartridge 21. This cross-section is represented in FIG. 8. The staple 23 is stretched over an interior 27 which is downstream of the interior between the adaptation surfaces 26, so that the tissue brought together by means of the adaptation surfaces 26 is located in the interior 27 and, therefore, between the staple 23. A cuboid-shaped closing element 28 is arranged on each of the two legs of a staple 23. The closing element 28 is, in each case, contacted by an axially extending pin 29, as a result of which the two closing elements 28 close the staple 23 due to pressure on the legs of the staple 23. Alternatively, the pins 29 can act directly on the staples 23.

The blades 15a and 15b and the staple cartridge 21 can be arranged extending axially behind each other. In addition, the blade or respectively the blades 15a and 15b can be fixedly connected to the guide rails 11 and the cutting insert 12 can move completely axially during the separation. It can additionally be provided that the staple cartridge 21 is fixedly connected to the plates 24 or respectively the guide rails 25 and during the clipping off or stapling is pushed forward completely along the guide rails 11. The rails 14 and 24 can also be configured as a fixed component of the clamping plates 3a and 3b, in which the blades 15a and 15b and the staple cartridge 21 extend as modules.

The staple insert 20 additionally comprises multiple channels 30 with openings 31 for providing a fluid, such as a coagulation-promoting or respectively fibrin-forming fluid. The channels 30 (in this example three channels 30 are configured, however one to approximately eight channels can be configured) extend in the axial direction, that is to say parallel to the plates 24. The openings 31 are configured perpendicularly to the axial direction and allow a supply of fluid to the resection surfaces. The openings 31 are each arranged in the staple cartridge 21 between two staples 23, as a result of which a good distribution of the fluid is guaranteed. This cross-section is represented in FIG. 9.

The handling of the device 1 for separating tissue parts will be described below with reference to FIGS. 10 to 12.

FIG. 10 shows the clamping of a tissue part 32 without squeezing between the two clamping plates 3a and 3b of the device 1. The tissue part 32 is then fixed, but not completely compressed.

The cutting insert 12 is then inserted with its plates 14 in the guide rails 11 of the clamping plates 3a and 3b and guided axially forwards in the direction of the tissue part 32 or respectively the clamping region 5. The cutting insert 12 can either be displaced manually or moved by means of the grip 6 or another actuation element of the grip part 2 in the direction of the clamping region 5. The cutting edge 16 is moved in the direction of the clamping region 5 with the movement of the cutting insert 12. The triangular blade 15 which is stretched between the two plates 14 then separates the tissue part 32 in the shape of a wedge by pushing forward axially.

The wedge-shaped tissue edges 32a are represented in FIG. 11. Following the separation of the tissue or respectively the tissue part 32, the remaining portion of the organ continues to be fixed between the clamping plates 3a and 3b. The cutting insert 12 is guided out axially and the resection surfaces can be inspected or respectively additionally supplied manually. After the cutting insert 12 is removed from the clamping plates 3a and 3b, the staple insert 20 is inserted in the clamping plates 3a and 3b. The staple insert 20 is pushed forward axially sufficiently far until the staple cartridge 21 and, therefore, the staples 23 are arranged in the clamping region 5 and, therefore, on or respectively above the tissue part 32.

During the forward movement, the adaptation surfaces 12 of the staple insert 20 bring together the tissue edges 32a following the wedge-shaped resection, wherein the staples 23 are stretched over the tissue edges 32 which have been brought together. This state is represented in FIG. 12. For stapling, the pins 29 are then pushed forward axially so that the staples 23 close by means of the closing elements 28. At the same time, coagulation-promoting or respectively fibrin-forming fluids are injected via the channels 30. The result is a complete invagination of the resection surface and sealing of potential erosion sites.

The staple insert 20 is subsequently removed in the axial direction from the clamping plates 3a and 3b. The pivotable part 3c of the clamping plate 3b is then opened and, consequently, the remaining organ or tissue part 32 is released.

The invention claimed is:

1. A device for separating tissue parts, the device comprising:
    a first clamping plate and a second clamping plate that are parallel with respect to each other, wherein at least one part of the first clamping plate is pivotable away from the second clamping plate to receive a tissue part and pivotable back to fix the tissue part; and
    a V-shaped blade having two partial blades and a cutting edge, wherein each of the two partial blades has a blade body and a cutting surface, the cutting surfaces of the two partial blades form the cutting edge of the V-shaped blade, the V-shaped blade has a length defined between the cutting edge and an end of the V-shaped blade disposed opposite with respect to the cutting edge, the cutting surfaces of the two partial blades meet each other at an intersection point, the blade bodies of the two partial blades are arranged at an angle α with respect to each other to form the V-shaped blade having a V-shaped cross-section at a point along the length of the V-shaped blade between the intersection point and the end of the V-shaped blade, the angle α is between 40° and 150°, the two partial blades are insertable and displaceable in guide rails of the first and second clamping plates, and the cutting edge of the V-shaped blade extends between the first and second clamping plates.

2. The device according to claim 1, wherein the two partial blades are fixedly or displaceably arranged in a cutting insert that is insertable and displaceable in the guide rails of the first and second clamping plates.

3. The device according to claim 2, wherein the cutting insert has recesses in the region facing away from the cutting edge of the V-shaped blade.

4. The device according to claim 2, wherein the cutting insert has a base body which is insertable in the guide rails of the first and second clamping plates and is displaceable in the latter, and which has receptacles for fastening or displaceably receiving the two partial blades.

5. The device according to claim 2, wherein the angle α and the V-shaped blade are configured such that the V-shaped blade is arranged in a V-shape between two plates of the cutting insert.

6. The device according to claim 1, wherein the angle α is 90°.

7. The device according to claim 1, wherein the intersection point is set back or placed in front with respect to outer ends of the two partial blades.

8. The device according to claim 1, wherein the two partial blades have a power connection and/or a connection for an ultrasound unit for thermal coagulation and/or ultrasonic dissection.

9. The device according to claim 1, further comprises a staple cartridge having staples arranged perpendicularly or at a different angle with respect to the first and second clamping plates.

10. The device according to claim 9, wherein the staple cartridge is directly insertable and displaceable in the guide rails.

11. The device according to claim 9, wherein the staple cartridge is fixedly or displaceably arranged in a staple insert, wherein the staple insert is insertable and displaceable in the guide rails.

12. The device according to claim 11, wherein the staple insert has pins extending parallel to the first and second clamping plates for closing, wherein the pins are displaceably arranged for contacting the staples or the pins contact the staples via closing elements.

13. The device of claim 11, wherein the staple insert has at least one channel with openings for providing a fluid or a granulate.

14. The device according to claim 9, wherein the staple cartridge has at least one channel with openings for providing a fluid or a granulate.

15. The device according to claim 9, wherein the staples are arranged under tension and can be independently closed after being released.

16. The device according to claim 9, wherein the two partial blades and the staple cartridge are arranged axially behind each other in the guide rails.

17. The device according to claim 1, further comprising a grip part, to which the first and second clamping plates are fastened and a grip of the grip part is set up to pivot the at least one part of the first clamping plate.

18. The device according to claim 1, wherein a distance of the pivotable part of the first clamping plate from the second clamping plate is adjustable.

19. The device according to claim 1, wherein an articulation which can be angled is provided in the region of the first and second clamping plates.

20. The device according to claim 1, wherein the two partial blades are directly insertable and displaceable in the guide rails.

* * * * *